United States Patent
Al-Shammari et al.

(10) Patent No.: US 9,156,929 B2
(45) Date of Patent: Oct. 13, 2015

(54) BIS(2-INDENYL) METALLOCENE COMPLEX

(71) Applicant: Saudi Basic Industries Corporation, Riyadh (SA)

(72) Inventors: Haif Al-Shammari, Riyadh (SA); Jason Morton, Thuwal (SA); Douglas Stephan, Toronto (CA)

(73) Assignee: SABIC INNOVATIVE PLASTICS IP B.V. (NL)

( * ) Notice: Subject to any disclaimer, the term of this patent is extended or adjusted under 35 U.S.C. 154(b) by 0 days.

(21) Appl. No.: 14/205,530

(22) Filed: Mar. 12, 2014

(65) Prior Publication Data
US 2014/0275455 A1 Sep. 18, 2014

Related U.S. Application Data

(60) Provisional application No. 61/927,084, filed on Jan. 14, 2014.

(30) Foreign Application Priority Data

Mar. 12, 2013 (EP) .................................. 13001242

(51) Int. Cl.
| | | |
|---|---|---|
| C07F 17/00 | (2006.01) | |
| C08F 4/6592 | (2006.01) | |
| C08F 210/00 | (2006.01) | |
| C08F 210/16 | (2006.01) | |
| C08F 4/659 | (2006.01) | |

(52) U.S. Cl.
CPC ............. *C08F 210/16* (2013.01); *C07F 17/00* (2013.01); *C08F 4/65927* (2013.01); *C08F 4/65912* (2013.01); *C08F 4/65916* (2013.01)

(58) Field of Classification Search
CPC ...... C07F 17/00; C08F 4/65927; C08F 10/00; C08F 210/16
See application file for complete search history.

(56) References Cited

U.S. PATENT DOCUMENTS

| 2,952,697 A | 9/1960 | Gorsich |
| 4,003,712 A | 1/1977 | Miller |
| 4,962,262 A | 10/1990 | Winter et al. |
| 2005/0137364 A1 | 6/2005 | Cai et al. |

FOREIGN PATENT DOCUMENTS

| EP | 0653445 A1 | 5/1995 |
| EP | 0786466 B1 | 1/1997 |
| WO | 9635729 | 11/1996 |
| WO | 0001736 | 1/2000 |

OTHER PUBLICATIONS

Benzing, Erhard, et al. "dialkylamido titanium (IV) chloride and alcoholates" Monsanto Research SA, Zurich 3 (Switzerland), 1961. Chemische Berichte, 1961, 94, 2263.
Donovan, Patrick et al. "Elaboration of Diaryl Ketones into Naphthalenes Fused on Two or Four Sides: A Naphthoannulation Procedure", JACS, 2004, 126, pp. 3108-3112.
Extended European Search report for EP13001242.0-1451, mailed Jun. 6, 2013, 4 pages.
Firme, Caio L. et al. : "Topological study of bis (cyclopentadienyl) titanium and bent titanocenes", Chemical Physics Letters, 499 (4-6), 193-198 Code: CHPLBC; ISSN: 0009-2614, 2010, XP002697676, p. 195 left paragraph.
McEwen, Ian et al. "Hydrogen Bonding of Hydroxy Groups to Carbanions in Indenide and Fluorenide Derivatized Alcohols Directly Observed by UV, IR, and . . . ", J. Am. Chem. Soc. 1993, 115, pp. 3989-3996.
Pangborn, A. B. et al. "Safe and Convenient Procedure for Solvent Purification", Organometallics 1996, 15, p. 1518.
Paul, G.C. et al. "Unexpected Coupling Reaction of 9-Lithiobromomethylene-9H-fluorene with 6,6-Dicyclopropylfulvene", Synthesis, May, 1997, pp. 524-526.
Randall, J.C., "A Review of High Resolution Liquid Carbon Nuclear Magnetic Resonance Characterizations of Ethylene-Based Polymers", Journal of Macromolecular Science, vol. C29, 2&3, 1989, pp. 285-297.
Rezaei, Hadi et al. "Preparation of 1-Bromo-1-chloro-, 1,1-Dibromoor 1, 1-Dichloroalk-1-enes from Ketones", Synthesis, 2000, pp. 109-111.
Modern Methods of Polymer Characterization, Edited by Howard G. Barth et al. 1991 by John Wiley & Sons, Chapter 3, Rudin, A., pp. 103-112.

(Continued)

*Primary Examiner* — Caixia Lu
(74) *Attorney, Agent, or Firm* — Cantor Colburn LLP

(57) ABSTRACT

The invention relates to a metallocene complex according to the following formula (1)

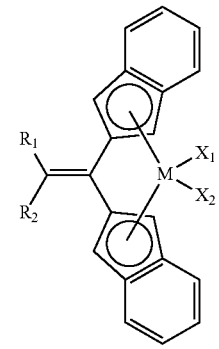

wherein $R_1$ and $R_2$ are the same or different and are a substituted or unsubstituted, linear or branched, hydrocarbyl group comprising 1 to 30 carbon atoms; M is titanium, zirconium, or hafnium and $X_1$ and $X_2$ are the same and are halogen or a hydrocarbyl group comprising 1 to 20 carbon atoms.

14 Claims, No Drawings

(56) References Cited

OTHER PUBLICATIONS

Wang, C. et al. Synthesis, Structural Features, and Formation of Organometallic Derivates of C-Bridged Cp/Amido Titanium and Zirconium "CpCN-Constrained Geometry" Systems, Organometallics, 2005, 24, pp. 4760-4773.

Warren, Timothy H. et al. "1,3-Doubly Bridged Group 4 Megallocenes by Intramolecular Reductive Coupling of Pendant Olefins", Organometallics 2000, 19, p. 127-134.

Zimm, Bruno H. et al. "The Dimensions of Chain Molecules Containing Branches and Rings", The Journal of Chemical Physics, vol. 17, No. 12, Dec. 1949, p. 1301.

BIS(2-INDENYL) METALLOCENE COMPLEX

The invention relates to a metallocene complex, a process to prepare a metallocene complex, a process to produce olefin polymers by polymerizing one or more olefins in the presence of a metallocene complex and to polyethylene, preferably linear low-density polyethylene, obtainable by copolymerizing ethylene and at least one other olefin, preferably 1-hexene in the presence of a metallocene complex.

Heterogeneous Ziegler-Natta titanium and Phillips chromium catalyst systems are currently utilized for the bulk of industrial linear polyethylene production. Great attention continues to be directed towards the synthesis and evaluation of homogeneous transition-metal catalysts. Such soluble, single-site metallocene catalysts are variable in their ligand scaffolding, allowing for the designed perturbation of the metal's electronic and structural environment. Soluble catalysts are of particular interest to complement the existing heterogeneous high- and low-density polyethylene (HDPE and LDPE) processes through the production of linear low-density polyethylene (LLDPE), where longer α-olefins such as 1-butene, 1-hexene, and 1-octene are incorporated into the polyethylene chain. LLDPE has a density lower than about 0.94 g/cm$^3$.

Group 4 ansa-metallocenes with a single atom bridge are particularly well-studied. An ansa-metallocene is an organometallic compound containing two cyclopentadienyl-containing ligands that are linked by a bridging group such that both cyclopentadienyl groups are bound to the same metal. The link prevents rotation of the cyclopentadienyl ligands and often modifies the structure and reactivity of the metal center. Examples of such ansa metallocene catalysts are described in EP0653445A, EP0786466A, WO96/35729, and WO00/01736. In the last patent publication metallocene complexes of the general formula R"(CpR$_m$)(Cp'R'$_n$)MQ2 are described, wherein Cp is a cyclopentadienyl moiety, Cp' is a substituted or unsubstituted fluorenyl ring, R" is a structural bridge imparting stereorigidity to the component, each R is independently a hydrocarbyl having 1 to 20 carbon atoms in which $0 \leq m \leq 4$, each R' is independently hydrocarbyl having 1 to 20 carbon atoms in which $0 \leq n \leq 8$, M is a group IVB transition metal or vanadium and each Q is hydrocarbyl having 1 to 20 carbon atoms or halogen; the metallocene having a centroid-M-centroid angle in the range 105° to 125°. In the metallocene complexes according to WO00/01736 the bridge between the two Cp moieties is an alkylidene bridge having 1 to 20 carbon atoms, a dialkyl germanium or dialkyl silicone or siloxane bridge, an alkyl phosphine or alkyl amine.

SUMMARY

The metallocene complexes according to the invention are metallocene complexes according to the following formula (1)

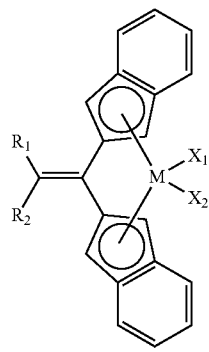

(1)

wherein R$_1$ and R$_2$ are the same or different and are independently a substituted or unsubstituted linear or branched hydrocarbyl groups comprising 1 to 30 carbon atoms; M is titanium, zirconium, or hafnium and X$_1$ and X$_2$ are the same and are halogen or a hydrocarbyl group comprising 1 to 20 carbon atoms.

The bridge in the metallocene complexes comprises a single, unsaturated carbon atom. This single unsaturated carbon atom in the bridge of the metallocene complexes surprisingly has the effect that LLDPE can be obtained with a high molecular weight and a high comonomer incorporation.

DETAILED DESCRIPTION

The metallocene complexes described herein include a complex according to the following formula (1)

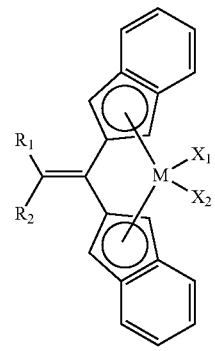

(1)

In this complex R$_1$ and R$_2$ are the same or different and are independently a substituted or unsubstituted, linear or branched, hydrocarbyl groups comprising 1 to 30 carbon atoms.

The hydrocarbyl groups may be aliphatic or aromatic. The hydrocarbyl groups may also be cyclic in which case the hydrocarbyl groups preferably comprise 3 to 30 carbon atoms. Preferably, R$_1$ and R$_2$ are linear hydrocarbyl groups, for example alkyl groups or cyclic aromatic hydrocarbyl groups comprising 1 to 30 carbon atoms. In some embodiments, R$_1$ and R$_2$ are linear hydrocarbyl groups, for example alkyl groups comprising 1 to 10 carbon atoms. Examples of these linear alkyl groups are methyl, ethyl, propyl, for example n-propyl, butyl, for example n-butyl and hexyl, for example n-hexyl.

In another embodiment, R$_1$ and R$_2$ are cyclic aromatic hydrocarbyl groups comprising 1-20 carbon atoms. Examples of these cyclic aromatic hydrocarbyl groups are substituted and unsubstituted aryl groups, for example phenyl groups, indenyl groups or fluorenyl groups. R$_1$ and R$_2$ may also form a ring together with the carbon atom to which they are bound to form a 5 or 6-membered ring which may be substituted or unsubstituted, for example R$_1$ and R$_2$ may form an indenyl or a fluorenyl group, preferably fluorenyl together with the carbon atom to which they are bound.

Preferably, R$_1$ and R$_2$ are selected from alkyl groups having 1 to 30 carbon atoms, for example from alkyl groups having 1 to 10 carbon atoms, for example R$_1$ and R$_2$ may be selected from the group of methyl, ethyl, n-propyl, n-butyl, n-pentyl, n-hexyl, phenyl, 1-indenyl and 2-indenyl.

More preferably, R$_1$ and R$_2$ are the same. Most preferably, R$_1$ and R$_2$ are chosen from the group of n-propyl, n-butyl, n-pentyl, and n-hexyl. In the metallocene complex according to the invention M is chosen from titanium (Ti), zirconium (Zr), or hafnium (Hf). Preferably, M is titanium In the metallocene complex $X_1$ and $X_2$ are preferably the same and are halogen or a hydrocarbyl group comprising 1 to 20 carbon atoms, for example a linear alkyl group comprising 1 to 20 carbon atoms or a cyclic aromatic group comprising 3 to 20 carbon atoms, for example an aryl group, for example phenyl. Preferably, $X_1$ and $X_2$ are each independently methyl and halogen, preferably Cl or Br, more preferably Cl. More preferably, $X_1$ and $X_2$ are the same and both stand for methyl or for a halogen, even more preferably $X_1$ and $X_2$ both stand for Cl or for Br, even more preferably $X_1$ and $X_2$ both stand for Cl.

The metallocene complex can be supported on a support. The support is preferably an inert support, more preferably a porous inert support. Examples of porous inert supports materials are talc and inorganic oxides. Preferably, the support material is in a finally divided form.

Therefore, the invention also relates to a composition comprising the metallocene complex wherein the metallocene complex is present on a support.

Suitable inorganic oxide materials include group 2A, 3A, 4A, and 4B metal oxides such as silica, alumina, and mixtures thereof. Other inorganic oxides that may be employed either alone or in combination with the silica or alumina are magnesia, titania, zirconia and the like. Other support materials, however, can be employed, for example finely divided functionalized polyolefins such as finely divided polyethylene.

Preferably, the support is a silica having a surface area between 200 and 900 m²/g and a pore volume between 0.5 and 4 ml/g.

The invention further relates to a process for the preparation of a metallocene complex (1), comprising
  a. transforming 2-bromoindene to the corresponding Grignard reagent 2-indenylMgBr;
  b. reacting 2-indenylMgBr with tri-n-butyltin chloride to give $(2-C_9H_7)Sn(n-butyl)_3$;
  c. reacting $(2-C_9H_7)Sn(n-butyl)_3$ with $Br_2C=CR_1R_2$ under Pd catalyzed conditions to form ligand precursors;
  d. creating anions of the ligand precursors with sodium hexamethyldisilazine; and
  e. reacting the anion of the ligand precursor with $(Me_2N)_2MCl_2$, wherein M is titanium (Ti), zirconium (Zr) or hafnium (Hf) and thereafter with trimethylsilylchloride, to yield a metallocene complex according to claim 1.

The process steps a-e are also shown in Scheme 1.

Scheme 1.

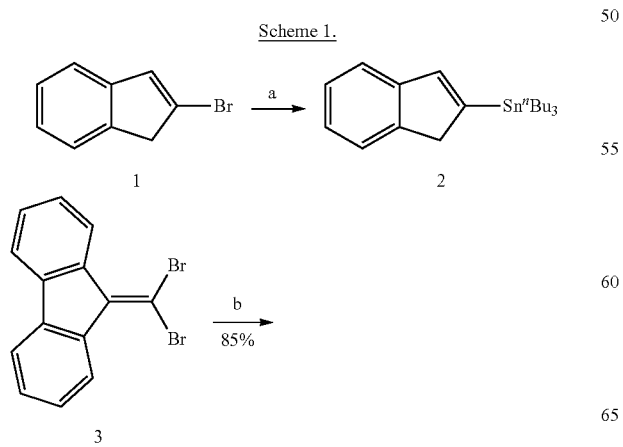

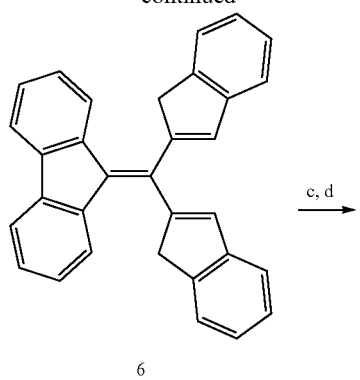

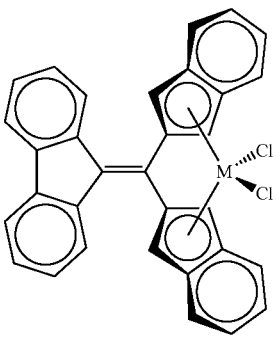

M = Ti: 9a, 89%
Zr: 9b, 48%

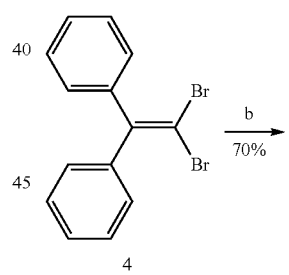

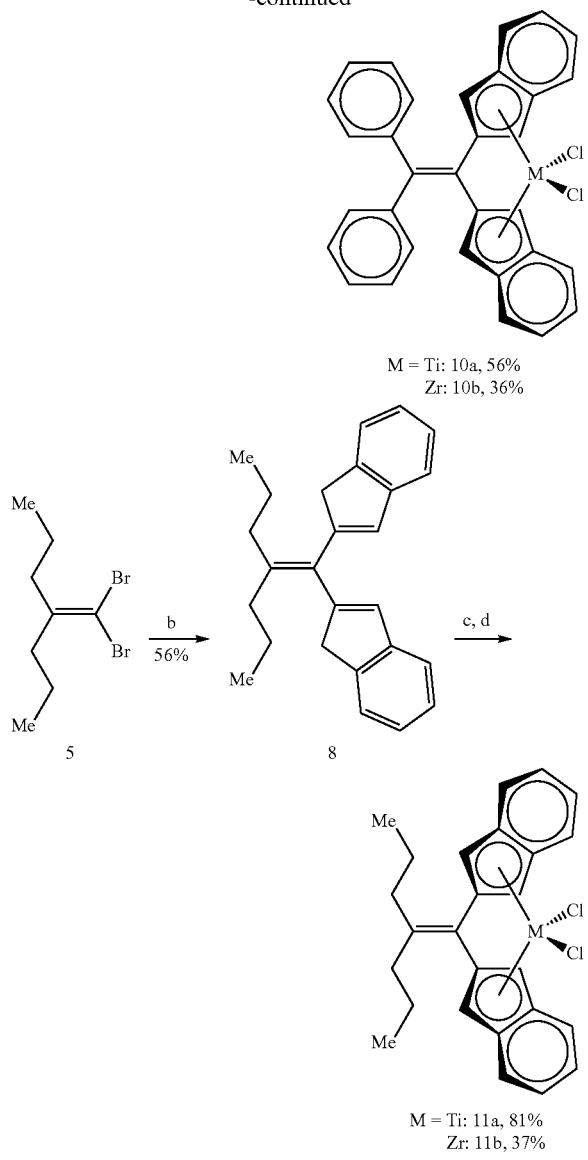

In another aspect, the invention relates to a process for the preparation of olefin polymers by polymerizing one or more olefins in the presence of the metallocene complex of the invention or in the presence of the composition of the invention, wherein the metallocene complex is present on a support and a cocatalyst The cocatalyst can include aluminium- or boron-containing cocatalysts. Suitable aluminium-containing cocatalysts comprise aluminoxanes and alkyl aluminium. The aluminoxanes are well known an preferably comprise oligomeric linear and/or cyclic alkyl aluminoxanes represented by the formula: $R^3$—$(AlR^3$—$O)_n$—$AlR^3{}_2$ for oligomeric, linear aluminoxanes and (—$AlR^3$—$O$—$)_m$ for oligomeric, cyclic aluminoxanes; wherein n is 1-40, preferably n is 10-20; m is 3-40, preferably m is 3-20 and $R^3$ is a $C_1$ to $C_8$ alkyl group and preferably a methyl group. Further other organoaluminum compounds can be used such as trimethylaluminum, triethylaluminium, triisopropylaluminum, tri-n-propylaluminum, triisobutylaluminum, tri-n-butylaluminum, triamylaluminium; dimethylaluminium ethoxide, diethylaluminium ethoxide, diisopropylaluminium ethoxide, di-n-propylaluminium ethoxide, diisobutylaluminium ethoxide and di-n-butylaluminium ethoxide; dimethylaluminium hydride, diethylaluminium hydride, diisopropylaluminium hydride, di-n-propylaluminium hydride, diisobutylaluminium hydride and di-n-butylaluminium hydride.

Suitable boron-containing cocatalysts are trialkylboranes, for example trimethylborane or triethylborane.

In the process to produce olefin polymers by polymerizing one or more olefins in the presence of a metallocene complex preferably an organoaluminum cocatalyst is present.

More preferably, methylaluminoxane is used as the cocatalyst.

The process to produce the olefin polymers preferably starts with the reaction of the metallocene complex according to the invention with the cocatalyst. This reaction can be performed in the same vessel as the reaction vessel wherein the olefin polymers are produced or in a separate vessel, whereafter the mixture of the metallocene complex and the cocatalyst is fed to the reaction vessel. During the reaction described above an inert solvent can be used.

In the mixture of the metallocene complex and the cocatalyst, the cocatalyst is used in an amount of 10 to 100,000 mol, preferably from 10 to 10,000 mol per mol of the transition metal compound.

The solvent used in the process to produce olefin polymers may be any organic solvent usually used for the polymerization. Examples of solvents are benzene, toluene, xylene, butane, pentane, hexane, heptane, and cyclohexane and methylene chloride. Also the olefin to be polymerized can be used as the solvent.

In the process to produce olefin polymers the polymerization conditions, like for example temperature, time, pressure, monomer concentration can be chosen within wide limits. The polymerization temperature is in the range from −100 to 300° C., preferably 0 to 200° C., more preferably 10 to 100° C. The polymerization time is in the range of from 10 seconds to 20 hours, preferably from 1 minute to 10 hours, more preferably from 5 minutes to 5 hours. The ethylene pressure during polymerization is in the range from 1 to 3500 bar, preferably from 1 to 2500 bar, more preferably from 1 to 1000 bar, even more preferably from 1 to 500 bar, most preferably from 1 to 100 bar. The molecular weight of the polymer can be controlled by use of hydrogen in the polymerization. The polymerization may be conducted by a batch process, a semi-continuous process, or a continuous process and may also be conducted in two or more steps of different polymerization conditions. The polyolefin produced is separated from the polymerization solvent and dried by methods known to a person skilled in the art.

In the process to produce olefin polymers the olefin which is polymerized can be one type of olefin or can be combinations of different olefins. The polymerization thus includes homopolymerization and copolymerization. Examples of olefins are α-olefins such as ethylene, propylene, 1-butene, 1-pentene, 4-methyl-1-pentene, 1-hexene, 1-octene, 1-nonene, 1-decene and styrene; conjugated and non-conjugated dienes such as butadiene, 1,4-hexadiene, 5-ethylidene-2-norbornene, dicyclopentadiene, 4-methyl-1,4-hexadiene and 7-methyl-1,6-octadiene; and cyclic olefins such as cyclobutene, but is not limited thereto.

Preferably, at least one of the olefins that is polymerized is ethylene. More preferably, a mixture of ethylene and at least one other olefin is polymerized. The other olefin is preferably chosen from 1-butene, 1-hexene, or 1-octene, more preferably the other olefin is 1-hexene.

In particular, in the production of LLDPE obtained by copolymerizing ethylene and an olefin of three or more carbon atoms a high molecular weight of the olefin polymer can be obtained. Preferably, the olefin of three or more carbon atoms is 1-butene, 1-hexene, or 1-octene, more preferably the other olefin is 1-hexene.

Preferably, the olefin comonomer is present in an amount of about 5 to about 20 percent by weight of the ethylene-olefin copolymer, more preferably an amount of from about 7 to about 15 percent by weight of the ethylene-alpha olefin copolymer.

For example an LLDPE having a melt mass flow rate (also known as melt flow index) as determined using ASTM D1238-10 (190° C./2.16 kg) which ranges from 4 to 125 g/10 min and a density in the range from 900 kg/m$^3$ to less than 940 kg/m$^3$ as determined using ASTM D1505-10 may be obtained. For example, the density of the linear low density polyethylene ranges from about 915 kg/m$^3$ to less than 940 kg/m$^3$.

Preferably, the melt flow index of the linear low density polyethylene ranges from 0.3 to 3 g/10 min, for example from 0.5 to 1.5 g/10 min. For purpose of the invention, the melt flow index is determined herein using ISO1133:2011 (190° C./2.16 kg).

The polymerization may be performed via a gas phase process or via a slurry process.

Gas fluidized bed polymerization processes are summarized by Than Chee Mun in Hydrocarbons 2003 "Production of polyethylene using gas fluidised bed reactor." Gas phase polymerization generally involves adding gaseous monomers into a vertically oriented polymerization reactor filled with previously formed polymer, catalyst particles, and additives. Generally the polymerization in the gas phase polymerization systems takes place at temperatures between 30° C. and 130° C. with super atmospheric pressures. The rising gas phase fluidizes the bed, and the monomers contained in the gas phase polymerize onto supported catalyst or preformed polymer during this process. Upon reaching the top of the reactor, unreacted monomer is recycled, while polymer continually falls down along the sides of the reactor. Examples of suitable gas phase polymerizations are disclosed in for example US-A-4003712 and US-A-2005/0137364.

In slurry reactors, a low boiling hydrocarbon solvent such as isobutane, hexane or heptane is employed as a continuous medium, and monomer, catalyst etc. is added to this continuous phase. The polymer formed is insoluble in the reaction medium, producing slurry of polymer and catalyst. Slurry reactors may be divided into loop reactors and boiling solvent reactors. Heat is at least partially removed by the heat of vaporization of solvent, which is later condensed and returned to the reactor. Polymer is removed as slurry from the bottom of the reactor and flashed to remove solvent, which is recycled. Slurry loop reactors may be horizontally or vertically oriented. Water flowing between the tubes serves to remove heat and maintain a relatively constant temperature. Slurry flow is achieved by pumps which maintain the polymer slurry at relatively high velocity. Product is removed either continuously or discontinuously from a "settling leg." Preferably, the polymerization with the metallocene complex according to the invention is a polymerization via a slurry process.

Hydrogen gas may also be added to the polymerization reactor(s) to control the final properties (e.g., 121 and/or 12) of the polyethylene composition. In some embodiments, the ratio of hydrogen to total ethylene monomer (ppm $H_2$/mol % $C_2$) in the circulating gas stream is in a range of from 0 to 60:1 in some embodiments; from 0.10:1 (0.10) to 50:1 (50) in another embodiment; from 0 to 35:1 (35) in another embodiment; from 0 to 25:1 (25) in another embodiment; from 7:1 (7) to 22:1 (22).

The invention is also directed to a polyolefin, for example polyethylene, preferably LLDPE or LDPE obtainable or obtained by the process of the invention, for example by copolymerizing ethylene and at least one other olefin in the presence of a metallocene complex according to the invention or a composition, wherein the metallocene complex is present on a support according to the invention.

As defined herein, in linear low density polyethylene, the term "linear" means that the polymer lacks measurable or demonstrable long chain branches, that is, the polymer is substituted with an average of less than 0.01 long chain branch/1000 carbon atoms.

"Long chain branching" (LCB) means a chain length longer than the short chain branch that results from the incorporation of the α-olefin(s) into the polymer backbone. Each long chain branch will have the same comonomer distribution as the polymer backbones and can be as long as the polymer backbone to which it is attached.

As a practical matter, current $^{13}$C nuclear magnetic resonance spectroscopy cannot distinguish the length of a long chain branch in excess of six carbon atoms. However, there are other known techniques useful for determining the presence of long chain branches in ethylene polymers. Two such methods are gel permeation chromatography coupled with a low angle laser light scattering detector (GPC-LALLS) and gel permeation chromatography coupled with a differential viscometer detector (GPCDV). The use of these techniques for long chain branch detection and the underlying theories have been well documented in the literature.

See, for example, Zimm, G. H. and Stockmayer, W. H., J. Chem. Phys., 17, 1301 (1949) and Rudin, A., Modern Methods of Polymer Characterization, John Wiley & Sons, New York (1991 pp. 103-112).

It has been found that with the metallocene complex of the invention or with the composition of the invention wherein the metallocene complex of the invention on a support, it is possible to produce polyethylene from ethylene and at least one other olefin, for example an olefin having up to 8 carbon atoms, with a high incorporation of the at least one other olefin.

The amount of incorporation of the at least one other olefin, for example an α-olefin in the polyethylene is expressed by the amount of branches per 1000 carbon atoms.

It has been found that in the polyethylene, for example LDPE or LLDPE of the invention, the amount of branches per 1000 carbon atoms is high.

The presence of short chain branching of up to 6 carbon atoms in length can be determined in ethylene polymers by using $^{13}$C nuclear magnetic resonance (NMR) spectroscopy and is quantified using the method described by Randall (Rev. Macromol. Chem. Phys., C.29, V. 2 & 3, p. 285-297).

Therefore, the invention also relates to a polyolefin, for example polyethylene, for example LDPE or LLDPE, having an amount of branches per 1000 carbon atoms as determined using $^{13}$C NMR of at least 18, for example of at least 18, for example at least 19, for example at least 20 and/or for example at most 30, for example at most 25, for example at most 23, for example at most 21. Preferably, said polyethylene is substituted with an average of less than 0.01 long chain branch per 1000 carbon atoms.

The number average molecular weight (Mn) of the polyolefin, for example polyethylene, for example LDPE or LLDPE of the invention may vary between wide ranges and may for example be in the range from 1000 to 200000 Da. For example, the Mn of the polyolefin of the invention may be at least 1500, for example at least 2000, for example at least 20,000, for example at least 50,000 and/or for example at most 150,000, for example at most 110,000, for example at most 100,000, for example at most 70,000.

The weight average molecular weight (Mw) of the polyolefin, for example polyethylene, for example LDPE or LLDPE of the invention may also vary between wide ranges and may for example be in the range from 1500 to 500000. For example, the Mw of the polyolefin of the invention may be at least 2500, for example at least 10,000, for example at least 50,000, for example at least 100,000 and/or for example at most 400,000, for example at least 350,000, for example at most 300,000, for example at most 250,000.

For purpose of the invention, the Mw and Mn are determined using SEC (Size Exclusion Chromatography using 1,2,4-trichlorobenzene as an eluent, and calibrated using linear polyethylene standards.

The molecular weight distribution (that is Mw/Mn) of the polyolefin of the invention may for example vary from 1.5 to 3.5, for example the molecular weight distribution (MWD) may range from 1.5 to 2.0 or from 2 to 3.5 or from 2.5 to 3.5.

The crystallinity temperature (Tc) of the polyolefin of the invention may for example be in the range from 90 to 120° C. The melt temperature ($T_m$) of the polyolefin of the invention may for example be in the range from 100 to 140° C.

For purpose of the invention, the $T_m$ and $T_c$ are determined using Differential Scanning calorimetry according to ASTM D 3418-08 using a scan rate of 10° C./min on a sample of 10 mg and using the second heating cycle The degree of crystallinity of the polyolefin of the invention may for example be in the range of 10 to 90%, for example at least 40% and/or for example at most 65%.

For purpose of the invention, the degree of crystallinity is determined using Differential Scanning calorimetry according to ASTM D 3418-08 using a scan rate of 10° C./min on a sample of 10 mg and using the second heating cycle.

The polyolefin obtained or obtainable by the process of the invention may be mixed with suitable additives.

Examples of suitable additives for polyethylene include but are not limited to the additives usually used for polyethylene, for example antioxidants, nucleating agents, acid scavengers, processing aids, lubricants, surfactants, blowing agents, ultraviolet light absorbers, quenchers, antistatic agents, slip agents, anti-blocking agents, antifogging agents, pigments, dyes and fillers, and cure agents such as peroxides. The additives may be present in the typically effective amounts well known in the art, such as 0.001 weight % to 10 weight % based on the total composition.

The polyolefins of the invention and compositions comprising said polyolefins may suitably be used for the manufacture of articles. For example, the polyolefins and compositions of the invention may be manufactured into film, for example by compounding, extrusion, film blowing or casting or other methods of film formation to achieve, for example uniaxial or biaxial orientation. Examples of films include blown or cast films formed by coextrusion (to form multilayer films) or by lamination and may be useful as films for packaging, for example as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets.

Therefore, in another aspect, the invention also relates to articles comprising the polyolefins obtainable by the process of the invention.

In yet another aspect, the invention also relates to use of the polyolefins obtainable by the process of the invention for the preparation of articles, for example for the preparation of films.

In yet another aspect, the invention relates to a process for the preparation of articles using the polyolefin according to the invention.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will hereafter be elucidated by way of the following examples, without being limited thereto.

EXAMPLES

Example I

Ligand Synthesis

This synthesis is also elucidated in Scheme 1.

To synthesize the ligands, 2-bromoindene (1) was first transformed to the corresponding Grignard reagent, then transmetallated with tri-n-butyltin chloride to give the stannane (2-$C_9H_7$)SnBu$_3$ (2). Migita-Kosugi-Stille cross-couplings with the gem-dibromides 3-5, were then accomplished under palladium-catalyzed conditions, providing the ligand precursors $R_2C$=C(2-$C_9H_7$)$_2$ (R =$C_{12}H_8$(6), Ph (7), n-Pr (8)). It is noteworthy that attempts to use 1H-inden-2-ylboronic acid or its trifluoroborate salt for this later transformation gave very low yields.

The ligand dianions were most effectively generated by deprotonation with sodium hexamethyldisilazine (NaHMDS). Though subsequent salt metathesis with the simple TiCl$_3$, TiCl$_4$, or ZrCl$_4$ gave inconsistent results, reactions with (Me$_2$N)$_2$TiCl$_2$ and (Me$_2$N)$_2$ZrCl$_2$.DME yielded the desired ansa-metallocenes. Finally, treatment with trimethylsilyl chloride provided the dichlorides $R_2C$=C(2-$C_9H_7$)$_2$MCl$_2$ (R=$C_{12}H_8$, M=Ti: 9a, Zr: 9b; R=Ph, M=Ti: 10a, Zr: 10b; R=n-Pr, M=Ti: 11 a, Zr: 11b) in yields ranging from 36-89%.

All complexes were characterized by $^1$H— and $^{13}$C-NMR spectroscopy and elemental analysis.

Compounds 2-bromoindene (1), 9-(dibromomethylene) fluorene (3), (2,2-dibromoethene-1,1-diyl)dibenzene (4), 4-(dibromomethylene)heptane (5), (Me$_2$N)$_2$ZrCl$_2$.2DME, and (Me$_2$N)$_2$TiCl$_2$ were prepared according to literature (See Mc Ewen, I.; Roennqvist, M.; Ahlberg, P. *J Am Chem Soc* 1993, 115, 3989; Paul, G. C.; Gajewski, J. J. *Synthesis* 1997, 524; Donovan, P. M.; Scott, L. T. *J. Am. Chem. Soc.* 2004, 126, 3108; Rezaei, H.; Normant, J. F. *Synthesis* 2000, 109. Warren, T. H.; Erker, G.; Fröhlich, R.; Wibbeling, B. *Organometallics* 2000, 19, 127; Benzing, E.; W., K. *Chem. Ber.* 1961, 94, 2263; Wang, C.; Erker, G.; Kehr, G.; Wedeking, K.; Fröhlich, R. *Organometallics* 2005, 24, 4760). All reactions were carried out and all metallocene complexes were manipulated under an atmosphere of anhydrous $N_2$ unless otherwise noted. Hexanes, iso-pentane, tetrahydrofuran (THF), diethyl ether ($Et_2O$), toluene (PhMe), and $CH_2Cl_2$ were dried and deoxygenated using a solvent purification system in the manner of Grubbs (Pangborn, A. B.; Giardello, M. A.; Grubbs, R. H.; Rosen, R. K.; Timmers, F. J. *Organometallics* 1996, 15, 1518), while benzene (PhH), chlorobenzene (PhCl), and 1-hexene were distilled from $CaH_2$. All solvents were degassed and held over 4 Å molecular sieves prior to use. All other reagents were commercially obtained and used as received. Preparative flash chromatography was performed on Kilocycle P6 40-63 μm silica gel. NMR analysis was obtained on Varian Mercury 400, Unity 500, and Brüker Avance III 400 spectrometers. Elemental analysis was performed by the University of Toronto, ANALEST facility, using a PerkinElmer 2400 Series II CHNS Analyzer.

Example II

Synthesis of $(C_9H_7)SnBu_3$ (2)

A Schlenk flask was charged with a magnetic stir bar and Mg turnings (5.6 g, 231 mmol, 3.0 eq.) and flame-dried under vacuum. After cooling, the flask was purged to $N_2$, anhydrous THF was added to just cover the turnings, and stirring was commenced. Two drops of 1,2-dibromoethane were added as initiator, and a heat gun used to briefly reflux the contents, after which the flask was placed in a 25° C. water bath. In a separate flame-dried flask under $N_2$ atmosphere, 2-bromoindene (1, 15.0 g, 76.9 mmol, 1.0 eq.) was dissolved in 75 mL anhydrous THF. A cannula was then used to transfer this solution onto the activated magnesium turnings over 45 min, resulting in a red, opaque solution. After 1.5 h, GC/MS analysis of an aliquot sample showed consumption of the 2-bromoindene. A separate flame-dried flask under $N_2$ atmosphere was charged with n-$Bu_3SnCl$ (22.9 mL, 84.6 mmol, 1.1 eq.) in 75 mL anhydrous THF and cooled to 0° C. To this was added, by cannula, the Grignard solution over 20 min., and the reaction flask was brought to ambient temperature for an additional 20 min. The mixture was quenched with chilled, saturated aq. $NH_4Cl$ and the organics were separated with $Et_2O$/brine three times. The combined organic layers were dried with anhydrous $MgSO_4$, filtered, and concentrated to an orange oil. This was pushed through a plug of activated, neutral alumina using hexanes, to provide, after removal of volatiles, the stannane 2 as a yellow oil (27.7 g, ~95 weight % purity by NMR) which was used without further purification. (The product is unstable to normal $SiO_2$ chromatography, while an attempt at vacuum distillation was unsuccessful). $^1$H-NMR (300 MHz, $CDCl_3$) δ 7.51 (d, J=7.3 Hz, 1H), 7.42 (d, J=7.4 Hz, 1H), 7.29 (t, J=7.3 Hz, 1H), 7.17 (td, J=7.4, 1.1 Hz, 1H), 7.09 (s, 1H), 3.52 (d, J=1.8 Hz, 2H), 1.79-1.49 (m, 6H), 1.47-1.29 (m, 6H), 1.11-1.12 (m, 6H), 0.94 (t, J=7.3 Hz, 9H). $^{13}$C-NMR (75 MHz, $CDCl_3$) δ 149.92, 147.00, 145.56, 141.81 ($J_{C-Sn}$=16.4 Hz), 126.06, 123.92, 123.21, 119.97, 45.85 ($J_{C-Sn}$=20.8, 20.0 Hz), 29.23 ($J_{C-Sn}$=10.5 Hz), 27.36 ($J_{C-Sn}$=28.5, 27.2 Hz), 13.69, 9.69 ($J_{C-Sn}$=173, 166 Hz).

Example III

Synthesis of $(C_{12}H_8)C=C(C_9H_7)_2$ (6)

In a flame-dried Schlenk flask under $N_2$ atmosphere were combined 9-(dibromomethylene)fluorene (3) (2.0 g, 5.95 mmol, 1.0 eq.) and tributyl(1H-inden-2-yl)stannane (2) (6.03 g, 14.9 mmol, 2.5 eq.). Magnetic stirring commenced, and the contents were degassed under vacuum for 15 min. The flask was purged with $N_2$, then charged with 30 mL anhydrous, degassed toluene. Tris(dibenzylideneacetone)dipalladium ($Pd_2(dba)_3$) (272 mg, 0.30 mmol, 0.05 eq.) and t-$Bu_3P$ (240 mg, 1.2 mmol, 0.2 eq.) were combined in 3 mL anhydrous, degassed toluene and syringed into the reaction mixture. This was followed by three freeze-pump-thaw cycles, then reintroduction of $N_2$ atmosphere. The reaction mixture was then heated at 100° C. for 14 h. After this time, the solution was allowed to cool to ambient temperature, and KF (3.46 g, 59.5 mmol, 10 eq.) and 30 mL $H_2O$ were added and the resultant biphasic mixture was stirred vigorously for 1 h. The crude product was then filtered through Celite, with ethylacetate (EtOAc) as additional eluant. After aqueous separation with brine, the organic layer was dried with $MgSO_4$ and concentrated by rotary evaporation onto 2 g of silica. Column chromatography (5→10→20→30% PhMe/hexanes; the product can be seen as a red band) provided the desired 6 (2.05 g, 85% yield) as a bright red solid. $^1$H-NMR (200 MHz, $CDCl_3$) δ 7.73 (d, J=7.5 Hz, 2H), 7.46 (dd, J=7.5, 5.2 Hz, 6H), 7.40-7.19 (m, 6H), 7.13-6.98 (m, 4H), 3.72 (s, 4H). $^{13}$C-NMR (101 MHz, $CDCl_3$) δ 148.45, 144.73, 143.99, 140.25, 138.49, 137.06, 134.96, 133.40, 127.67, 126.80, 125.35, 124.80, 123.96, 121.70, 119.49, 40.95. Analysis Calc'd for $C_{32}H_{22}$ (406.52 g/mol): C, 94.55; H, 5.45. Found: C, 94.08; H, 5.83.

Example IV

Synthesis of $Ph_2C=C(C_9H_7)_2$ (7)

In a flame-dried Schlenk flask under $N_2$ atmosphere were combined (2,2-dibromoethene-1,1-diyl)dibenzene (4) (1.0 g, 2.96 mmol, 1.0 eq.) and tributyl(1H-inden-2-yl)stannane (2) (3.00 g, 7.40 mmol, 2.5 eq.). Magnetic stirring was commenced, and the contents were degassed under vacuum for 15 min. The flask was purged with $N_2$, and then charged with 15 mL anhydrous, degassed toluene. $Pd_2(dba)_3$ (136 mg, 0.15 mmol, 0.05 eq.) and t-$Bu_3P$ (120 mg, 0.59 mmol, 0.2 eq.) were combined in 1.5 mL anhydrous, degassed toluene and syringed into the reaction mixture. This was followed by three freeze-pump-thaw cycles, then reintroduction of $N_2$ atmosphere. The reaction mixture was then heated at 100° C. for 14 h. After this time the solution was allowed to cool to ambient temperature, then KF (1.72 g, 29.6 mmol, 10 eq.) and 15 mL $H_2O$ were added and the resultant biphasic mixture was stirred vigorously for 1 h. The crude product was then filtered through Celite, with ethyl acetate (EtOAc) as additional eluant. After aqueous separation with brine, the organic layer was dried with $MgSO_4$ and concentrated by rotary evaporation onto 3 g of silica. Column chromatography (5→10→20→30→40% PhMe/hexanes; the product can be seen as a yellow band) provided the desired 7 (840 mg, 70% yield) as a bright yellow solid. $^1$H-NMR (400 MHz, $CDCl_3$) δ 7.43-7.27 (m, 16H), 7.24 (td, J=7.2, 1.5 Hz, 2H), 6.84 (s, 2H), 3.34 (s, 2H). $^{13}$C-NMR (101 MHz, $CDCl_3$) δ 150.00, 144.61, 143.86, 143.77, 141.27, 134.11, 133.06, 130.45, 128.06, 126.98, 126.23, 124.54, 123.36, 120.86, 41.25. Analysis Calc'd for $C_{32}H_{24}$ (408.53 g/mol): C, 94.08; H, 5.92. Found: C, 93.61; H, 6.21.

Example V

Synthesis of n-$Pr_2C=C(C_9H_7)_2$ (8)

In a flame-dried Schlenk flask under $N_2$ atmosphere were combined 4-(dibromomethylene)heptane (5) (1.0 g, 3.70 mmol, 1.0 eq.) and tributyl(1H-inden-2-yl)stannane (2) (3.75 g, 9.26 mmol, 2.5 eq.). Magnetic stirring commenced, and the contents were degassed under vacuum for 15 min. The flask was purged with $N_2$, then charged with 18.5 mL anhydrous, degassed toluene. $Pd_2(dba)_3$ (169 mg, 0.185 mmol, 0.05 eq.) and t-$Bu_3P$ (150 mg, 0.74 mmol, 0.2 eq.) were combined in 1 mL anhydrous, degassed toluene and syringed into the reaction mixture. This was followed by three freeze-pump-thaw cycles, then reintroduction of $N_2$ atmosphere. The reaction mixture was then heated at 100° C. for 20 h. After this time, the solution was allowed to cool to ambient temperature, and KF (2.15 g, 37.0 mmol, 10 eq.) and 20 mL $H_2O$ were added and the resultant biphasic mixture was stirred vigorously for 1 h. The crude product was then filtered through Celite, with EtOAc as additional eluant. After aqueous separation with brine, the organic layer was dried with $MgSO_4$ and concentrated by rotary evaporation onto 2 g of silica. Column chromatography (5% PhMe/hexanes) provided the desired 8 (704 mg, 56% yield) as a slightly yellow, viscous oil. $^1$H-NMR (400 MHz, $CDCl_3$) δ 7.30 (d, J=7.4 Hz, 1H), 7.23 (dd, J=14.1, 7.3 Hz, 2H), 7.11 (td, J=7.4, 1.1 Hz, 1H), 6.64 (s, 1H), 3.26 (s, 2H), 2.36-2.04 (m, 2H), 1.56-1.36 (m, 2H), 0.84 (t, J=7.3 Hz, 3H). $^{13}$C-NMR (100 MHz, $CDCl_3$) δ 148.78, 145.60, 143.65, 141.13, 130.83, 129.89, 126.80, 124.66, 123.85, 121.04, 42.51, 34.94, 22.53, 14.31. Analysis Calc'd for $C_{26}H_{28}$ (340.50 g/mol): C, 91.71; H, 8.29. Found C, 91.30; H, 8.40.

Example VI

Synthesis of $(C_{12}H_8)C=C(C_9H_6)_2TiCl_2$ (9a)

In the glovebox, under $N_2$ atmosphere, a vial was charged with 9-(di(1H-inden-2-yl)methylene)fluorene (6) (73 mg, 0.180 mmol, 1.0 eq.) and 3.6 mL THF. The mixture was stirred magnetically and cooled to −35° C., after which time solid NaHMDS (69 mg, 0.377 mmol, 2.1 eq.) was added in one portion. The reaction was allowed to warm slowly to ambient temperature and stirred for a total time of 5 h. The homogenous solution was then cooled back to −35° C. and solid $(Me_2N)_2TiCl_2$ (39.1 mg, 0.189 mmol, 1.05 eq.) was added. The reaction mixture was allowed to warm slowly to ambient temperature and stirred overnight. After this time, the THF was removed in vacuo. The residue was filtered through Celite with PhH, concentrated, and washed with 2 mL portions of pentanes (5 times) to remove trace remaining $(Me_2N)_2TiCl_2$. The resultant dark purple residue was dissolved in 1.5 mL $CH_2Cl_2$, after which $Me_3SiCl$ (0.06 mL, 0.46 mmol, 3.0 eq.) was added. The reaction mixture was stirred magnetically for 12 h, then the volatiles were removed in vacuo. The purple residue was added to a small pipet packed with Celite. It was washed with PhH, which was then discarded. The remaining solids were then filtered through using PhCl, which after concentration and precipitation from hexanes provided 9a (38 mg, 48% yield) as a purple solid. Crystals suitable for X-ray diffraction could be grown by vial-in-vial solvent diffusion of a concentrated solution of 9a in PhCl with hexanes. $^1$H-NMR (500 MHz, $C_6D_5Br$) δ 7.84 (d, J=7.7 Hz, 2H), 7.81 (d, J=7.6 Hz, 2H), 7.73 (dd, J=6.5, 3.1 Hz, 4H), 7.47 (dt, J=7.6, 1.1 Hz), 7.30 (dd, J=6.4, 3.1 Hz, 2H), 7.17 (dt, J=7.6, 1.1 Hz, 2H), 6.24 (s, 4H). $^{13}$C-NMR (partial, by gHMBC; $C_6D_5Br$) δ 141.5, 137.4, 133.9, 130.0, 128.4, 127.9, 126.3, 125.3, 120.7, 113.1, 109.4. Analysis Calc'd for $C_{32}H_{20}Cl_2Ti.C_6H_5Cl$ (634.05 g/mol): C, 71.78; H, 3.96. Found: C, 71.92; H, 4.39.

Example VII

Synthesis of $Ph_2C=C(C_9H_6)_2TiCl_2$ (10a)

In the glovebox, under $N_2$ atmosphere, a vial was charged with 2,2'-(2,2-diphenylethene-1,1-diyl)bis(1H-indene) (7) (147 mg, 0.360 mmol, 1.0 eq.) and 7.2 mL THF. The mixture was stirred magnetically and cooled to −35° C., after which time solid NaHMDS (139 mg, 0.756 mmol, 2.1 eq.) was added in one portion. The reaction was allowed to warm slowly to ambient temperature and stirred for a total time of 4 h. The homogenous solution was then cooled back to −35° C. and solid $(Me_2N)_2TiCl_2$ (78 mg, 0.378 mmol, 1.05 eq.) was added. The reaction mixture was allowed to warm slowly to ambient temperature and stirred overnight. After this time, the THF was removed in vacuo. The residue was washed over a plug of Celite with hexanes, and the eluant discarded. The remaining residue was then washed through with PhH. The solvent was removed and the yellow/brown solid taken up in 2.4 mL $CH_2Cl_2$, after which trimethylsilylchloride (0.091 mL, 0.720 mmol, 3.0 eq.) was added. The reaction mixture was stirred magnetically for 12 h, then the volatiles were removed in vacuo. The dark residue was added to a small pipet packed with Celite. It washed with a 3:1 pentane/$Et_2O$ solution, which was then discarded. The remaining solids were then filtered through using $CH_2Cl_2$, which after concentration provided 10a (68 mg, 36% yield) as a purple solid. Crystals suitable for X-ray diffraction could be grown by layering hexanes over a concentrated solution of 10a in $CH_2Cl_2$. $^1$H-NMR (400 MHz, $CD_2Cl_2$) δ 7.58-7.53 (m, 4H), 7.49 (dd, J=6.5, 3.1 Hz, 4H), 7.40-7.26 (m, 10H), 6.18 (s, 4H). $^{13}$C-NMR (101 MHz, $CD_2Cl_2$) δ 144.60, 139.39, 133.72, 130.41, 128.92, 128.87, 128.78, 128.11, 127.16, 126.07, 114.83, 110.89. Analysis Calc'd for $C_{32}H_{22}Cl_2Ti.CH_2Cl_2$ (612.24): C, 64.95; H, 3.96. Found: C, 64.43; H, 3.84.

Example VIII

Synthesis of n-$Pr_2C=C(C_9H_6)_2TiCl_2$ (11a)

In the glovebox, under $N_2$ atmosphere, a vial was charged with 2,2'-(2-propylpent-1-ene-1,1-diyl)bis(1H-indene) (8) (206 mg, 0.605 mmol, 1.0 eq.) and 12 mL THF. The mixture was stirred magnetically and cooled to −35° C., after which time solid NaHMDS (233 mg, 1.27 mmol, 2.1 eq.) was added in one portion. The reaction was allowed to warm slowly to ambient temperature and stirred for a total time of 6 h. The homogenous solution was then cooled back to −35° C. and solid $(Me_2N)_{2TiCl2}$ (131 mg, 0.635 mmol, 1.05 eq.) was added. The reaction mixture was allowed to warm slowly to ambient temperature and stirred overnight. After this time, the THF was removed in vacuo. The residue was washed through a plug of Celite with hexanes, providing a red solid after removal of the solvent in vacuo. This residue was then dissolved in 3.2 mL $CH_2Cl_2$, after which $Me_3SiCl$ (0.12 mL, 0.980 mmol, 3.0 eq.) was added. The reaction mixture was stirred magnetically for 12 h, and then the volatiles were removed in vacuo. The dark residue was added to a small pipet packed with Celite and filtered through using $CH_2Cl_2$. Removal of solvent in vacuo, then washing/decanting the resultant purple solid with pentanes (three times) provided 11a (130 mg, 47% yield) as a purple solid. Crystals suitable for X-ray diffraction were grown by vial-in-vial solvent diffusion of a concentrated solution of 11 a in $CH_2Cl_2$ with hexanes. $^1$H-NMR (400 MHz, $C_6D_6$) δ 7.47 (dd, J=6.4, 2.9 Hz, 4H), 7.01 (dd, J=6.4, 2.9 Hz, 4H), 5.65 (s, 4H), 2.19 (t, J=7.4 Hz, 4H), 1.59-1.34 (m, 4H), 0.86 (t, J=7.3 Hz, 6H). $^{13}$C-NMR (101 MHz, $C_6D_6$) δ □ 142.37, 133.49, 127.81, 125.71, 125.34, 114.60, 109.56, 33.16, 21.40, 13.99. Analysis Calcd for $C_{26}H_{26}Cl_2Ti$ (457.26): HC, 68.29; H, 5.73. Found: C, 68.15; H, 5.88.

Example IX

Synthesis of (C$_{12}$H$_8$)C=C(C$_9$H$_6$)$_2$ZrCl$_2$ (9b)

In the glovebox, under N$_2$ atmosphere, a vial was charged with 9-(di(1H-inden-2-yl)methylene)fluorene (6) (92 mg, 0.226 mmol, 1.0 eq.) and 4.5 mL THF. The mixture was stirred magnetically and cooled to −35° C., after which time solid NaHMDS (91.3 mg, 0.498 mmol, 2.2 eq.) was added in one portion; the reaction mixture immediately went to a deep purple color. The reaction was allowed to warm slowly to ambient temperature and stirred for a total time of 5 h. The homogenous solution was then cooled back to −35° C. and solid (Me$_2$N)$_2$ZrCl$_2$. DME (81 mg, 0.237 mmol, 1.05 eq.) was added. The reaction mixture was allowed to warm slowly to ambient temperature and stirred overnight. After this time, the THF was removed in vacuo. The brown residue was filtered through Celite with PhH and concentrated. The resulting solid was dissolved in 2.3 mL CH$_2$Cl$_2$, after which Me$_3$SiCl (0.09 mL, 0.86 mmol, 3.0 eq.) was added. The reaction mixture was stirred magnetically at ambient temperature for 12 h, during which time red precipitates crash out. The volatiles were removed in vacuo, and the residue washed with 2 mL Et$_2$O, then 6 mL hexanes. The supernatant was decanted off, and the residue washed with further 6 mL portions of hexanes (three times) to provide, after removal of trace solvent in vacuo, the desired 9b (114 mg, 89% yield) as an orange, highly insoluble solid. Crystals suitable for X-ray diffraction were grown by slow precipitation of a PhMe/PhH solution. $^1$H-NMR (400 MHz, C$_6$D$_6$) δ 7.60 (d, J=7.7 Hz, 2H), 7.53 (d, J=7.6 Hz, 2H) 7.50 (dd, J=6.5, 3.1 Hz, 4H), 7.16 (dt, J=1.0, 7.6 Hz), 6.97 (dd, J=3.1, 6.5 Hz, 4H), 6.88 (dt, J=1.1, 7.6 Hz, 2H), 5.68 (s, 4H). $^{13}$C-NMR (100 MHz, C$_6$D$_6$) δ 141.3, 137.4, 129.5, 129.2, 128.5, 127.6, 127.1, 126.9, 125.3, 125.0, 120.3, 116.6, 101.7. Analysis Calc'd for C$_{32}$H$_{22}$Cl$_2$Zr.C$_6$H$_5$Cl (681.20 g/mol): C, 67.20; H, 3.71. Found: C, 66.90; H, 4.07.

Example X

Synthesis of Ph$_2$C=C(C$_9$H$_6$)$_2$ZrCl$_2$ (10b)

In the glovebox, under N$_2$ atmosphere, a vial was charged with 2,2'-(2,2-diphenylethene-1,1-diyl)bis(1H-indene) (7) (255 mg, 0.624 mmol, 1.0 eq.) and 12.5 mL THF. The mixture was stirred magnetically and cooled to −35° C., after which time solid NaHMDS (252 mg, 1.37 mmol, 2.2 eq.) was added in one portion; the reaction mixture immediately took on a deep red coloration. The reaction was allowed to warm slowly to ambient temperature and stirred for a total time of 5.5 h. The homogenous solution was then cooled back to −35° C. and solid (Me$_2$N)$_2$ZrCl$_2$. DME (223 mg, 0.655 mmol, 1.05 eq.) was added. The reaction mixture was allowed to warm slowly to ambient temperature and stirred overnight. After this time, the THF was removed in vacuo. The residue was filtered through Celite with PhH and concentrated. The resultant residue was dissolved in 3 mL CH$_2$Cl$_2$, after which Me$_3$SiCl (0.28 mL, 1.87 mmol, 3.0 eq.) was added. The reaction mixture was stirred magnetically for 12 h, and then the volatiles were removed in vacuo. The resulting residue was dissolved in CH$_2$Cl$_2$, after which time slow addition of hexanes causes precipitation of the desired complex. The supernatant was decanted, and the procedure repeated, to give 10b (200 mg, 56%) as a yellow powder. Crystals suitable for X-ray diffraction were grown by layering a concentrated solution of 10b in CH$_2$Cl$_2$ with pentane. $^1$H-NMR (400 MHz, C$_6$D$_6$) δ 7.57-7.47 (m, 4H), 7.39 (dd, J=6.5, 3.1 Hz, 4H), 7.10-6.93 (m, 6H), 6.90 (dd, J=6.5, 3.1 Hz, 4H), 5.62 (s, 4H). $^{13}$C-NMR (100 MHz, C$_6$D$_6$) δ 144.39, 139.64, 130.27, 128.67, 128.54, 128.51, 128.26 (found by gHMBC) 126.57, 124.86, 117.73, 102.64. Analysis Calcd for C$_{32}$H$_{22}$Cl$_2$.C$_6$H$_5$Cl (681.20): C, 67.00; H, 4.00. Found: C, 67.19; H, 4.38.

Example XI

Synthesis of n-Pr$_2$C=C(C$_9$H$_6$)$_2$ZrCl$_2$ (11b)

In the glovebox, under N$_2$ atmosphere, a vial was charged with 2,2'42-propylpent-1-ene-1,1-diyl)bis(1H-indene) (8) (130 mg, 0.382 mmol, 1.0 eq.) and 7.6 mL THF. The mixture was stirred magnetically and cooled to −35° C., after which time solid NaHMDS (147 mg, 0.802 mmol, 2.1 eq.) was added in one portion. The reaction was allowed to warm slowly to ambient temperature and stirred for a total time of 5.5 h. The homogenous solution was then cooled back to −35° C. and solid (Me$_2$N)$_2$ZrCl$_2$. DME (137 mg, 0.401 mmol, 1.05 eq.) was added. The reaction mixture was allowed to warm slowly to ambient temperature and stirred overnight. After this time, the THF was removed in vacuo. The residue was filtered through Celite with pentanes and the solvent removed in vacuo. The resultant green/yellow residue was dissolved in 3.7 mL CH$_2$Cl$_2$, after which trimethylsilylchloride (0.14 mL, 1.1 mmol, 3.0 eq.) was added. The reaction mixture was stirred magnetically for 12 h, then the volatiles were removed in vacuo. The orange residue was washed with 5:1 pentane/Et$_2$O to remove impurities, then filtered through Celite with PhH and concentrated to provide 11b as a yellow solid (155 mg, 81% yield). $^1$H-NMR (400 MHz, C$_6$D$_6$) δ 7.47 (dd, J=6.5, 3.1 Hz, 4H), 6.97 (dd, J=6.5, 3.1 Hz, 4H), 5.57 (s, 4H), 2.24-2.15 (m, 4H), 1.59-1.35 (m, 4H), 0.86 (t, J=7.4 Hz, 6H). $^{13}$C-NMR (101 MHz, C$_6$D$_6$) δ 143.01, 129.08, 126.53, 125.70, 124.88, 118.16, 102.54, 33.09, 21.47, 13.98. Analysis Calcd for C$_{26}$H$_{26}$Cl$_2$Zr (500.61): C, 62.38; H, 5.23. Found: C, 62.23; H, 5.41.

Example XII

Comparative Examples

The following known metallocene complexes were used for the comparative polymerization examples:

A—biphenyl bis(2-indenyl)zirconium dichloride

B—1,2-Ethylene bis(9-fluorenyl)zirconium dichloride

C—rac-Ethylene bis(indenyl)zirconium dichloride

D—rac-1,2-Ethylene bis(4,5,6,7-tetrahydro-1-indenyl)zirconium dichloride

E—rac-dimethylsily bis(tetrahydro-1-indenyl)zirconium dichloride

Polymerization: About 1 mg of each complexes 9a, 10a, 11a, 9b, and 10b, A, B, C, D, and E was suspended in 5 ml toluene. Methylalumoxane (10% in toluene, M:Al=1:1500) was added to the suspended complex in toluene. After around two minutes shaking, the mixture was transferred under inert atmosphere to a 2 liter autoclave reactor filled with 250 ml of iso-pentane, 100 ml of 1-hexene, and thermostatted at 60° C. An ethylene pressure of 20 bar was applied for 1 hour. After releasing the pressure, the polymer was filtered through an airless filter funnel, washed with diluted hydrochloric acid, water, and acetone, and finally dried in vacuum. The polymerization results are presented in Table 1.

1-Hexene Copolymer Quantification: $^{13}$C-NMR analysis was performed at 130° C. on a Bruker 400 MHz NMR spectrometer. Polyethylene samples of 250 mg were kept in a sample vial and dissolved in o-dichlorobenzene (ODCB) at 130° C. The DMSO-$d_6$ was used as an internal lock having concentration 3:97 (v/v) with ODCB solvent. The acquired data were processed and analyzed using XWINNMR software version 3.5.

Gel Permeation Chromatography (GPC): measurements were performed using Waters Alliance GPC 2000 instrument. The polyethylene samples were dissolved in 1,2,4-trichlorobenzene (flow rate 1 ml/min) and measured at 150° C.

Density analysis: The density of the polyethylene samples was measured using a Tyoceiki automatic densitometer model DH-100.

Differential scanning calorimetry (DSC): The DSC test of the polyethylene samples was performed using TA Instruments Model Q2000 & Q1000.

flicts with a term in the incorporated reference, the term from the present application takes precedence over the conflicting term from the incorporated reference.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

TABLE 1

| Catalyst | Productivity (g PE/g Cat) | GPC Mn | GPC Mw (g/mol) | GPC MWD | DSC Tc (° C.) | DSC Tm (° C.) | DSC Crystallinity (%) | centroid-M-centroid angle (°) | Branch per 1000 C atoms | Density (g/ml) |
|---|---|---|---|---|---|---|---|---|---|---|
| 9a | 103000 | 94000 | 292500 | 3.11 | 113 | 127 | 59 | 121.84 | 13.67 | 0.9392 |
| 10a | 28000 | 106500 | 313000 | 2.94 | 115 | 129 | 54 | 121.07 | 17.68 | 0.9317 |
| 11a | 96000 | 55000 | 122500 | 2.23 | 110 | 122 | 49 | 121.67 | 20.51 | 0.9246 |
| 9b | 19000 | 1500 | 2700 | 1.8 | 98 | 106 | 53 | 117.02 | 15.56 | 0.9330 |
| 10b | 27000 | 1650 | 3100 | 1.9 | 100 | 109 | 54 | 115.97 | 14.95 | 0.9345 |
| A | 79000 | 167500 | 381000 | 2.27 | 117 | 131 | 62 | ND | 10.68 | 0.9398 |
| B | 111000 | 188000 | 497000 | 2.64 | 106 | 120 | 48 | 129.0 | 16.34 | 0.9189 |
| C | 46000 | 42500 | 108500 | 2.55 | 111 | 125 | 57 | 126.9 | 12.64 | 0.9355 |
| D | 54000 | 165500 | 495000 | 2.99 | 104 | 122 | 43 | 125.2 | 16.14 | 0.9218 |
| E | 50000 | 166500 | 480000 | 2.88 | 102 | 119 | 42 | 126.4 | 17.8 | 0.9182 |

ND = not determined

The above experiments show that with the use of the metallocene complexes according to the invention, LLDPE can be obtained with a high weight average molecular weight and a high amount of branches per 1000 C atoms.

The terms "a" and "an" do not denote a limitation of quantity, but rather denote the presence of at least one of the referenced item. The term "or" means "and/or." The endpoints of all ranges directed to the same component or property are inclusive of the endpoints, are independently combinable, and include all intermediate points and ranges. The term "combination" is inclusive of blends, mixtures, alloys, reaction products, and the like.

In general, the compositions or methods may alternatively comprise, consist of, or consist essentially of, any appropriate components or steps herein disclosed. The invention may additionally, or alternatively, be formulated so as to be devoid, or substantially free, of any components, materials, ingredients, adjuvants, or species, or steps used in the prior art compositions or that are otherwise not necessary to the achievement of the function and/or objectives of the present claims.

All cited patents, patent applications, and other references are incorporated herein by reference in their entirety. However, if a term in the present application contradicts or con-

What is claimed is:
1. A metallocene complex according to the following formula (1)

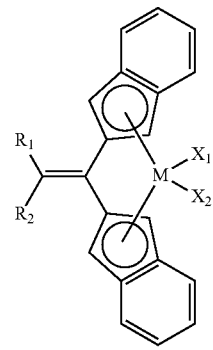

wherein
$R_1$ and $R_2$ are the same or different and are independently a substituted or unsubstituted, linear or branched, hydrocarbyl group comprising 1 to 30 carbon atoms;
M is titanium, zirconium, or hafnium; and
$X_1$ and $X_2$ are the same and are halogen or a hydrocarbyl group comprising 1 to 20 carbon atoms.

2. The metallocene complex according to claim 1, wherein $R_1$ and $R_2$ are selected from methyl, ethyl, n-propyl, n-butyl, n-pentyl, n-hexyl, phenyl, 1-indenyl, 2-indenyl or $R_1$ and $R_2$ form a ring together with the carbon atom to which they are bound to form a 5 or 6-membered ring which may be substituted or unsubstituted.

3. The metallocene complex according to claim 1, wherein $R_1$ and $R_2$ are the same.

4. The metallocene complex according to claim 3, wherein $R_1$ and $R_2$ are n-propyl, n-butyl, n-pentyl, or n-hexyl.

5. The metallocene complex according to claim 1, wherein M is Ti.

6. The metallocene complex according to claim 1, wherein $X_1$ and $X_2$ are Cl.

7. The metallocene complex according to claim 1, wherein the metallocene complex is present on a support.

8. A process for the preparation of a metallocene complex of claim 1, comprising
   a. transforming 2-bromoindene to the corresponding Grignard reagent 2-indenylMgBr;
   b. reacting 2-indenylMgBr with tri-n-butyltin chloride to give $(2\text{-}C_9H_7)Sn(n\text{-butyl})_3$;
   c. reacting $(2\text{-}C_9H_7)Sn(n\text{-butyl})_3$ with $Br_2C{=}CR_1R_2$ under Pd catalyzed conditions to form ligand precursors;
   d. creating anions of the ligand precursors with sodium hexamethyldisilazine; and
   e. reacting the anion of the ligand precursor with $(Me_2N)_2MCl_2$, wherein M is titanium (Ti), zirconium (Zr) or hafnium (Hf) and thereafter with trimethylsilylchloride, to yield a metallocene complex according to claim 1.

9. A process for the preparation of olefin polymers by polymerizing at least one olefin in the presence of the metallocene complex of claim 1 and a cocatalyst.

10. The process according to claim 9, wherein the metallocene complex of claim 1 is disposed on a support.

11. The process according to claim 9, wherein the at least one olefin is ethylene.

12. The process according to claim 9, wherein a combination of ethylene and at least one other olefin is used.

13. The process according to claim 11, wherein the other olefin is 1-butene, 1-hexene, or 1-octene.

14. The process according to claim 9, wherein an organoaluminum cocatalyst is present.

* * * * *